United States Patent
Ueda et al.

(10) Patent No.: US 12,121,213 B2
(45) Date of Patent: Oct. 22, 2024

(54) ENDOSCOPE AID AND ENDOSCOPE

(71) Applicant: FUJIFILM Corporation, Tokyo (JP)

(72) Inventors: Yoshihiro Ueda, Kanagawa (JP); Nobuyuki Torisawa, Kanagawa (JP); Shozo Iyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 652 days.

(21) Appl. No.: 17/105,631

(22) Filed: Nov. 27, 2020

(65) Prior Publication Data
US 2021/0076909 A1     Mar. 18, 2021

Related U.S. Application Data

(63) Continuation of application No. PCT/JP2019/024907, filed on Jun. 24, 2019.

(30) Foreign Application Priority Data

Jul. 19, 2018 (JP) .................. 2018-136170

(51) Int. Cl.
*A61B 1/00* (2006.01)
*A61B 1/005* (2006.01)
*A61B 1/018* (2006.01)

(52) U.S. Cl.
CPC ........ *A61B 1/0055* (2013.01); *A61B 1/00101* (2013.01); *A61B 1/0014* (2013.01); *A61B 1/018* (2013.01)

(58) Field of Classification Search
CPC ... A61B 1/00101; A61B 1/018; A61B 1/0055; A61B 1/00091; A61B 1/00094; A61B 1/00098
See application file for complete search history.

(56) References Cited

U.S. PATENT DOCUMENTS 4,669,172 A   6/1987 Petruzzi
4,967,732 A * 11/1990 Inoue ................ A61B 1/00137
                                              600/149
(Continued)

FOREIGN PATENT DOCUMENTS

CN      103027653      4/2013
CN      105852780      8/2016
(Continued)

OTHER PUBLICATIONS

"International Search Report (Form PCT/ISA/210) of PCT/JP2019/024907," mailed on Sep. 17, 2019, with English translation thereof, pp. 1-3.

(Continued)

*Primary Examiner* — Timothy J Neal
(74) *Attorney, Agent, or Firm* — JCIPRNET

(57) ABSTRACT

An endoscope aid 100 to be attachably and detachably attached to a treatment tool insertion channel 23 of an endoscope 2 includes a tubular member 101 capable of being fixed to an outlet portion 25 in a state where the tubular member 101 is fitted inside the outlet portion 25 of the treatment tool insertion channel 23 that is kept in the shape of a straight pipe regardless of bending of a bending part 15 of the endoscope 2. When the tubular member 101 is fixed to the outlet portion 25, a proximal end 101A of the tubular member 101 located on a side opposite to an outlet side of the treatment tool insertion channel 23 is disposed closer to the outlet side of the treatment tool insertion channel 23 than a proximal end 15A of the bending part 15.

20 Claims, 12 Drawing Sheets

(56) References Cited

U.S. PATENT DOCUMENTS

| | | | | |
|---|---|---|---|---|
| 5,261,391 | A | * | 11/1993 | Inoue ................. A61B 1/00137 600/153 |
| 5,797,958 | A | | 8/1998 | Yoon |
| 5,827,175 | A | | 10/1998 | Tanaka |
| 6,059,719 | A | * | 5/2000 | Yamamoto ....... A61B 17/00234 606/1 |
| 10,716,461 | B2 | * | 7/2020 | Jenkins .............. A61B 1/00105 |
| 11,246,472 | B2 | | 2/2022 | Takahashi et al. |
| 2010/0063480 | A1 | | 3/2010 | Shireman |
| 2017/0079505 | A1 | | 3/2017 | Nakade |
| 2017/0086652 | A1 | | 3/2017 | Nakade et al. |
| 2018/0078121 | A1 | | 3/2018 | Yasuda et al. |
| 2020/0187759 | A1 | | 6/2020 | Yamada et al. |

FOREIGN PATENT DOCUMENTS

| | | |
|---|---|---|
| CN | 106455925 | 2/2017 |
| CN | 106470589 | 3/2017 |
| JP | H1099336 | 4/1998 |
| JP | 2000342516 | 12/2000 |
| JP | 2001231746 | 8/2001 |
| JP | 2004261349 | 9/2004 |
| JP | 2006280772 | 10/2006 |
| WO | 2008127886 | 10/2008 |
| WO | 2018021583 | 2/2018 |

OTHER PUBLICATIONS

"Written Opinion of the International Searching Authority (Form PCT/ISA/237) of PCT/JP2019/024907," mailed on Sep. 17, 2019, with English translation thereof, pp. 1-12.

"Office Action of Japan Counterpart Application", issued on Dec. 14, 2021, with English translation thereof, p. 1-p. 10.

"Search Report of Europe Counterpart Application", issued on Jul. 20, 2021, pp. 1-7.

"Office Action of Europe Counterpart Application", issued on Dec. 20, 2022, p. 1-p. 5.

"Office Action of Japan Counterpart Application" with English translation thereof, issued on Apr. 12, 2022, p. 1-p. 10.

"Office Action of China Counterpart Application", issued on Nov. 7, 2023, with English translation thereof, p. 1-p. 13.

* cited by examiner

ENDOSCOPE AID AND ENDOSCOPE

CROSS-REFERENCE TO RELATED APPLICATIONS

This application is a Continuation of PCT International Application No. PCT/JP2019/024907 filed on Jun. 24, 2019, which claims priority under 35 U.S.C § 119(a) to Japanese Patent Application No. 2018-136170 filed on Jul. 19, 2018. Each of the above application(s) is hereby expressly incorporated by reference, in its entirety, into the present application.

BACKGROUND OF THE INVENTION

1. Field of the Invention

The present invention relates to an endoscope aid and an endoscope.

2. Description of the Related Art

A treatment tool insertion channel protective device described in JP2001-231746A has almost the same length as the length of a treatment tool insertion passage of an endoscope and comprises a flexible protective tube capable of being inserted into and removed from the treatment tool insertion passage, and a proximal end mouthpiece coupled to a proximal end of the protective tube. The proximal end mouthpiece is engageable with and disengageable from an inlet portion of the treatment tool insertion passage and has an inner hole that smoothly communicates with the protective tube.

An object to be inserted of an endoscope described in JP2004-261349A is inserted into a pipe line opening of an endoscope distal end part of a pipe line through which a fluid for cleaning an endoscope distal end surface is passed, and has an opening part on a side surface of a distal end part disposed so as to protrude from the pipe line opening. With an observation window, an illumination window, and the like as cleaning target parts, the object to be inserted is positioned such that the opening part faces the cleaning target parts.

SUMMARY OF THE INVENTION

The internal diameters of treatment tool insertion channels of endoscopes are variously different. For example, the internal diameter of a treatment tool insertion channel of an oral endoscope is larger than the internal diameter of a treatment tool insertion channel of a transnasal endoscope. The sizes of treatment tools are variously different. For example, there is a case where a treatment tool with a relatively small size is preferably used for the treatment that requires an accurate treatment tool operation. Here, in a case where the internal diameter of a treatment tool insertion channel is excessive with respect to the size of a treatment tool, the disposition of the treatment tool is not settled in an outlet portion of the treatment tool insertion channel, and the difficulty of treatment increases unnecessarily. On the other hand, changing endoscopes in accordance with treatment imposes a burden on a subject. Therefore, in one endoscope, the internal diameter of a treatment tool insertion channel is desired to be changed depending on situations.

The treatment tool insertion channel protective device described in JP2001-231746A is intended to insert and remove a treatment tool such as a puncture needle into and from the treatment tool insertion passage of the endoscope without obstruction. However, the internal diameter of the treatment tool insertion channel is changed by the protective tube having almost the same length as the length of the treatment tool insertion passage. However, the disposition of the protective tube in the outlet portion of the treatment tool insertion channel is not taken into consideration at all. In a case where the disposition of the protective tube is not stable at the outlet portion of the treatment tool insertion channel, the disposition of the treatment tool inserted through the protective tube is not stable. Moreover, the protective tube having almost the same length as the length of the treatment tool insertion passage is disposed over the entire length of the bending part of the endoscope. For this reason, the protective tube affects the bending of the bending part of the endoscope, and there is a concern that the bending performance such as the maximum bending angle degrades.

The object to be inserted of the endoscope described in JP2004-261349A is inserted into the pipe line opening of the endoscope distal end part of the pipe line through which the fluid for cleaning the endoscope distal end surface is passed, and is not attached to the pipe line opening of the treatment tool insertion channel and does not allow the treatment tool to be inserted therethrough.

The present invention has been made in view of the above-described circumstances, and an object thereof is to provide an endoscope aid capable of changing the internal diameter of a treatment tool insertion channel of an endoscope in accordance with situations while suppressing degradation of the bending performance of a bending part of the endoscope and capable of stabilizing the disposition of a treatment tool in the outlet portion of the treatment tool insertion channel, and an endoscope comprising a treatment tool insertion channel to which the endoscope aid is attachable.

An endoscope aid according to one aspect of the present invention is an endoscope aid to be attachably and detachably attached to a treatment tool insertion channel of an endoscope. The endoscope aid comprises a tubular member capable of being fixed to an outlet portion of the treatment tool insertion channel in a state where the tubular member is fitted inside the outlet portion of the treatment tool insertion channel that is kept in the shape of a straight pipe regardless of bending of a bending part of the endoscope. When the tubular member is fixed to the outlet portion of the treatment tool insertion channel, a proximal end of the tubular member located on a side opposite to an outlet side of the treatment tool insertion channel is disposed closer to the outlet side of the treatment tool insertion channel than a proximal end of the bending part of the endoscope.

Additionally, an endoscope of an aspect of the present invention comprises a treatment tool insertion channel to which the endoscope aid is attachable.

According to the present invention, it is possible to the endoscope aid capable of changing the internal diameter of the treatment tool insertion channel of the endoscope in accordance with situations while suppressing degradation of the bending performance of the bending part of the endoscope and capable of stabilizing the disposition of the treatment tool in the outlet portion of the treatment tool insertion channel, and it is possible to provide the endoscope comprising the treatment tool insertion channel to which the endoscope aid is attachable.

DESCRIPTION OF THE PREFERRED EMBODIMENTS

Figure 1:
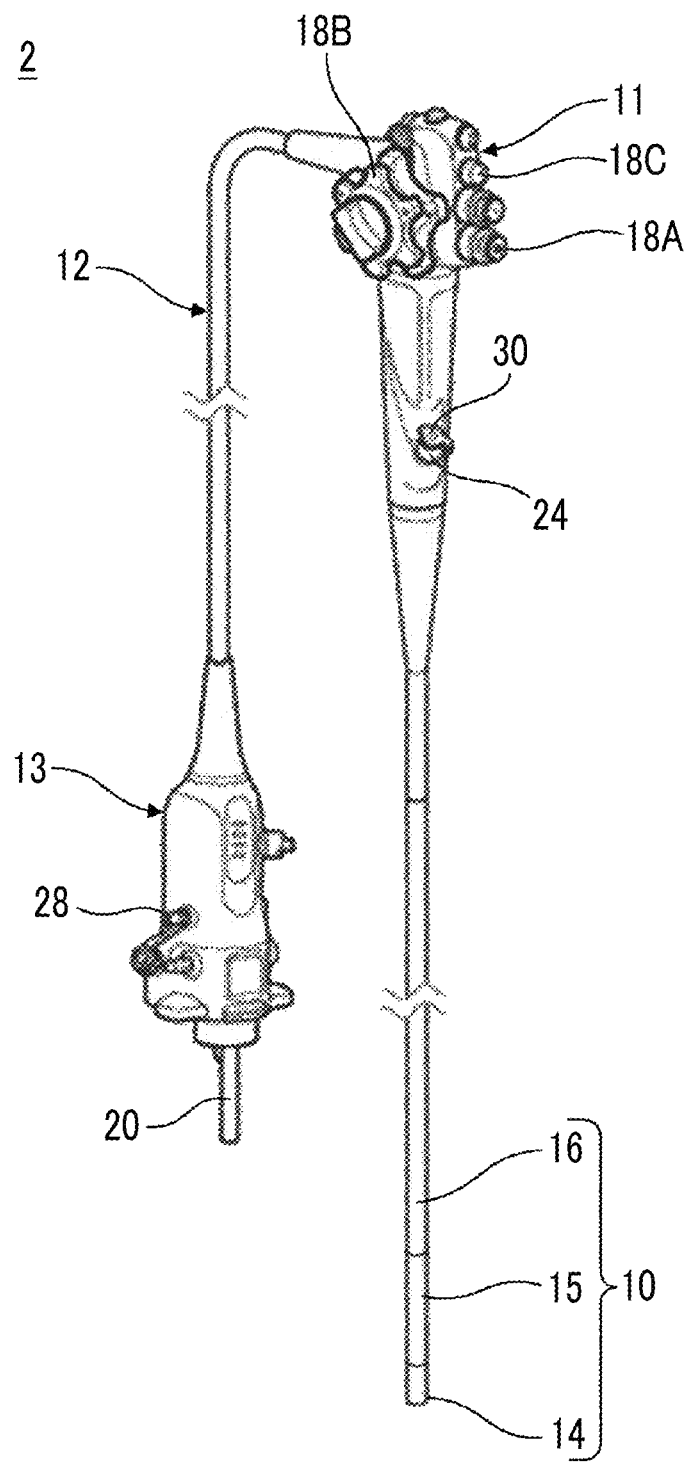
FIG. 1 is a perspective view of an example of an endoscope for explaining an embodiment of the present invention.
Figure 2:
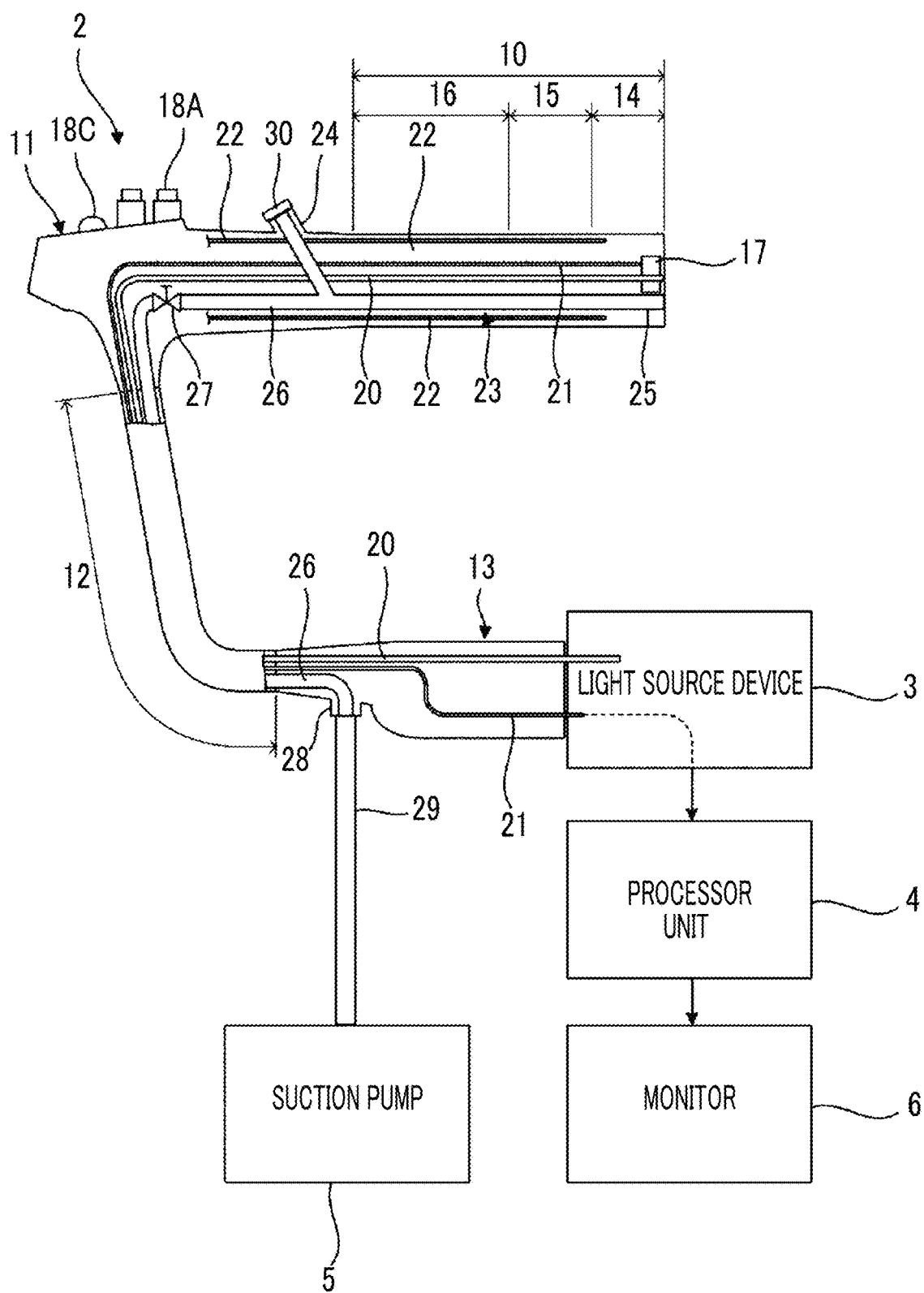
FIG. 2 is a schematic view of an example of an endoscope system including the endoscope of FIG. 1.

FIG. 1 illustrates an example of an endoscope for explaining an embodiment of the present invention, and FIG. 2 illustrates an example of an endoscope system including the endoscope of FIG. 1.

The endoscope system 1 comprises an endoscope 2, a light source device 3, a processor unit 4, and a suction pump 5. An endoscope 2 has an insertion part 10 to be inserted into a subject, an operating part 11 connected to the insertion part 10, and a universal cord 12 extending from the operating part 11, and a terminal of the universal cord 12 is provided with a connector 13 to be connected to the light source device 3.

The insertion part 10 of the endoscope 2 is constituted of a distal end part 14, a bending part 15 connected to the distal end part 14, and a flexible part 16 that connects the bending part 15 and the operating part 11 to each other. An imaging unit 17 including imaging elements, such as a charge coupled device (CCD) image sensor and a complementary metal oxide semiconductor (CMOS) image sensor, is mounted on the distal end part 14. The bending part 15 is configured to be bendable, and bending of the bending part 15 is operated by the operating part 11. Additionally, the flexible part 16 is configured to be flexible so as to be deformable along the shape of an insertion path of the subject.

The operating part 11 is provided with an operation button 18A that operates suction using the suction pump 5, an operating knob 18B that operates the bending of the bending part 15, an operation button 18C that operates imaging using the imaging unit 17, and the like. Additionally, the operating part 11 is provided with an inlet portion 24 of the treatment tool insertion channel 23 through which a treatment tool is inserted.

A light guide 20 and an electrical cable 21 are provided inside the insertion part 10, the operating part 11, and the universal cord 12. The light guide 20 guides illumination light, which is to be generated by the light source device 3, to the distal end part 14. The electrical cable 21 transmits operating power, control signals, and captured image signals of the imaging unit 17 between the imaging unit 17 and the processor unit 4. The processor unit 4 generates captured image data from input captured image signals, and causes the generated captured image data to be displayed on the monitor 6 and recorded.

A plurality of operating wires 22 and a treatment tool insertion channel 23 are provided inside the insertion part 10 and the operating part 11. The operating wires 22 reach the distal end part 14 of the insertion part 10 from the operating part 11, and are pushed toward the distal end part 14 or pulled toward the operating part 11 in accordance with the operation of the operating knob 18B of the operating part 11. The bending part 15 is bent in accordance with the push/pull of the operating wire 22. The treatment tool insertion channel 23 reaches the distal end part 14 of the insertion part 10 from the inlet portion 24 provided in the operating part 11, and an outlet portion 25 of the treatment tool insertion channel 23 opens to an end surface of the distal end part 14. A treatment tool inserted into the treatment tool insertion channel 23 through the opening of the inlet portion 24 is guided to the distal end part 14 of the insertion part 10 by the treatment tool insertion channel 23 and protrudes from the distal end part 14 through an opening of the outlet portion 25.

The treatment tool insertion channel 23 is bifurcated in the operating part 11, one of which is connected to the inlet portion 24 of the treatment tool insertion channel 23 and the other of which is connected to the suction tube 26. The suction tube 26 extends to the connector 13 via a valve 27 opened and closed by the operation button 18A and is connected to the suction pump 5 via the connection tube 29 connected to a mouthpiece 28 provided in the connector 13. By opening the valve 27, the treatment tool insertion channel 23 and the suction tube 26 communicate with each other, and the liquid, such as blood, is suctioned from the opening of the outlet portion 25 of the treatment tool insertion channel 23 to the suction pump 5. In addition, a forceps valve 30 having an on-off valve is mounted on the inlet portion 24, and as the opening of the inlet portion 24 is closed by the forceps valve 30 at the time of suction, the internal pressure of the treatment tool insertion channel 23 becomes negative pressure.

Figure 3:
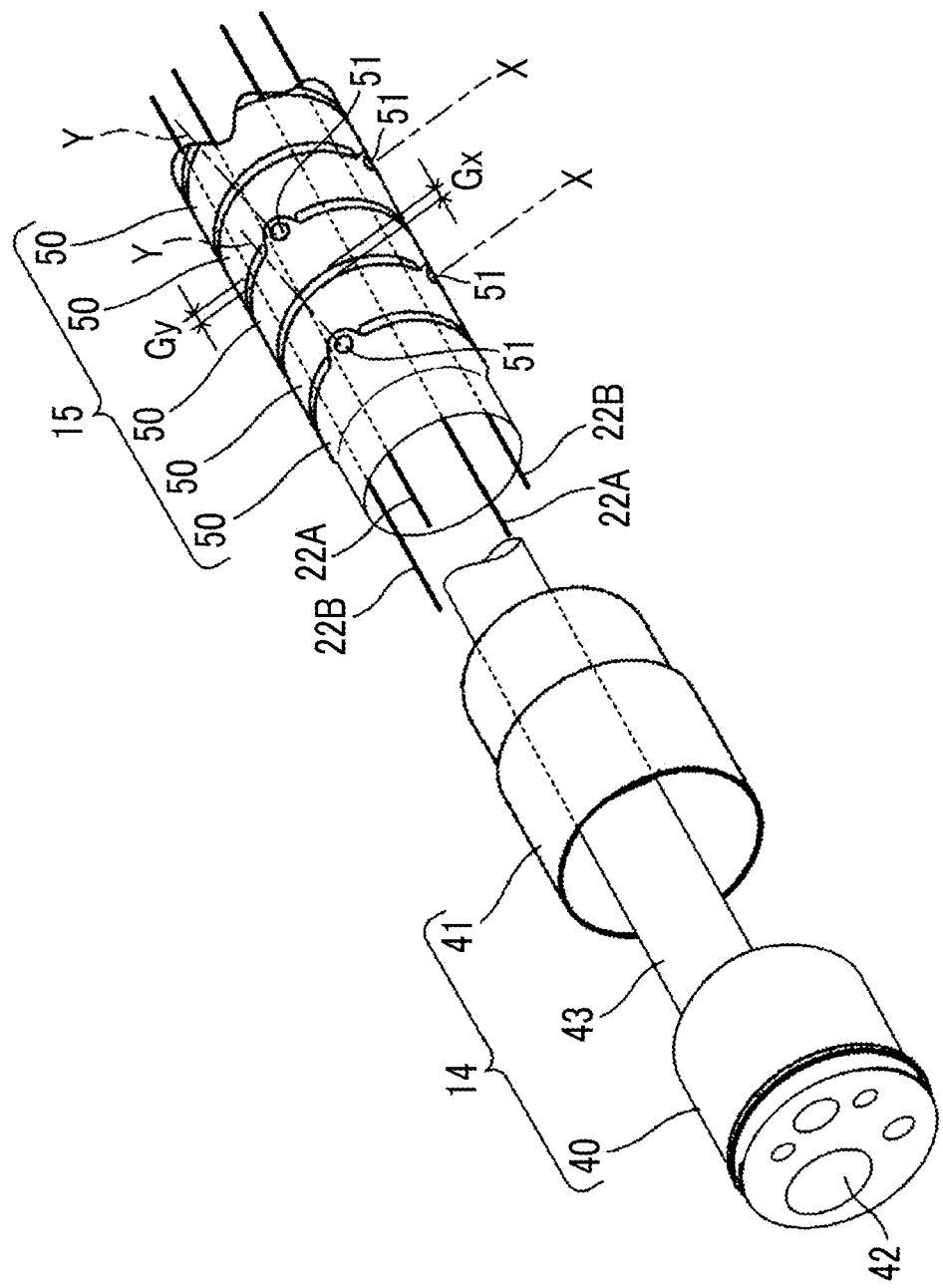
FIG. 3 is a perspective view illustrating an internal mechanism of a distal end part and a bending part in an insertion part of the endoscope of FIG. 1.

FIG. 3 illustrates an internal mechanism of the distal end part 14 and the bending part 15 of the insertion part 10.

The endoscope distal end part 14 has a columnar distal end rigid part 40 that holds various built-in elements, such as the imaging unit 17 (refer to FIG. 2), to be mounted on the distal end part 14, and a cylindrical distal end sleeve 41 to be fixed to a proximal end side of the distal end rigid part 40. A through-hole 42, which passes through the distal end rigid part 40 in an axial direction and has a circular cross-sectional shape, is formed in the distal end rigid part 40. A flexible channel tube 43, which constitutes the treatment tool insertion channel 23 and has a circular cross-sectional shape, is joined to the distal end rigid part 40. An inner hole of the channel tube 43 joined to the distal end rigid part 40, and the through-hole 42 communicate with each other, and the through-hole 42 constitutes at least a portion of the outlet portion 25 of the treatment tool insertion channel 23.

The bending part 15 of the endoscope has a plurality of annular pieces 50, and the pieces 50 are arranged with their central axes aligned with each other. A piece 50 disposed nearest to the distal end part 14 side among the plurality of pieces 50 is fixed to the distal end sleeve 41 of the distal end part 14. Two adjacent pieces 50 are coupled to each other so as to be rotationally movable by a pair of shaft members 51 disposed on an axis orthogonal to a longitudinal axis of the bending part 15. As the rotational movements of the two adjacent pieces 50 are combined together, the bending part 15 is bent as a whole.

In the example illustrated in FIG. 3, a rotational movement axis X and a rotational movement axis Y substantially perpendicular to the rotational movement axis X are alternately provided as rotational movement axes of the two adjacent pieces 50. The bending part 15 is capable of being bent in a total of four directions of upward-downward directions based on the rotational movement around the rotational movement axes X of the two adjacent pieces 50 and leftward-rightward directions based on the rotational movement around the rotational movement axes Y of the two adjacent pieces 50.

In addition, the maximum bending angle of the bending part 15 in the leftward-rightward directions and the maximum bending angle of the bending part 15 in the upward-downward directions may be the same as or different from each other. For example, the maximum bending angles in the upward-downward directions can be made relatively large by making the number of sets of two pieces 50 rotationally movable around the rotational movement axis X more than the number of sets of two pieces 50 rotationally movable around the rotational movement axis Y.

Additionally, the maximum rotational movement angles of respective sets of two pieces 50 rotationally movable around the rotational movement axis X may be the same as or different from each other, and the maximum rotational movement angle of each set can be set depending on a spacing Gx between the two pieces 50. Similarly, the maximum rotational movement angles of respective sets of two pieces 50 rotationally movable around the rotational movement axis Y may be the same as or different from each other, and the maximum rotational movement angle of each set can be set depending on a spacing Gy between the two pieces 50.

A pair of operating wires 22A corresponding to bending in the upward-downward directions and a pair of operating wires 22B corresponding to bending in the leftward-rightward directions are provided as the plurality of operating wires 22 (refer to FIG. 2). The pair of operating wires 22A and the pair of operating wires 22B reach the distal end part 14 from the operating part 11 through the insides of the plurality of pieces 50 and are fixed to the distal end sleeve 41, respectively. Additionally, the channel tube 43 that forms the treatment tool insertion channel 23 also reaches the distal end part 14 from the operating part 11 through the insides of the plurality of pieces 50 and is joined to the distal end rigid part 40.

Figure 4:
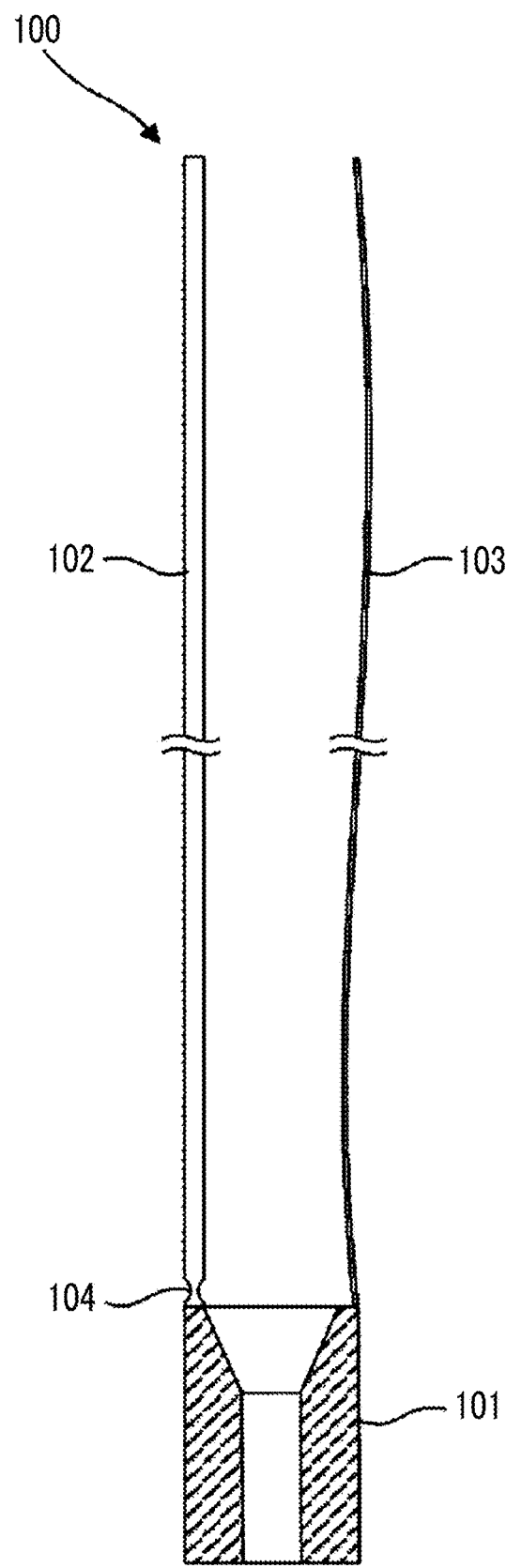
FIG. 4 is a plan view of an example of an endoscope aid for explaining the embodiment of the present invention.

FIG. 4 illustrates an example of the endoscope aid for explaining the embodiment of the present invention.

An endoscope aid 100 illustrated in FIG. 4 is attachably and detachably attached to the treatment tool insertion channel 23 of the endoscope 2. The endoscope aid 100 includes a tubular member 101 having a circular cross-sectional shape, a rod-shaped member 102 connected to a proximal end part of the tubular member 101, and a wire member 103 connected to a proximal end part of the tubular member 101.

The tubular member 101 is an elastic body containing an elastomer such as urethane rubber, silicone rubber, or fluororubber. The tubular member 101 is fixed to the outlet portion 25 in a state where the tubular member 101 is inserted into the treatment tool insertion channel 23 through an opening of the inlet portion 24 of the treatment tool insertion channel 23 and is fitted inside the outlet portion 25 of the treatment tool insertion channel 23. The external diameter of at least a portion the tubular member 101 in the axial direction is larger than the internal diameter of the outlet portion 25 of the treatment tool insertion channel 23, and the tubular member 101 is fixed inside the outlet portion 25 by being fitted inside the outlet portion 25 in a so-called interference fit state with elastic diameter-reducing deformation of a portion having a larger diameter than the outlet portion 25. In addition, on the example illustrated in FIG. 4, the entire external diameter of the tubular member 101 in the axial direction is larger than the internal diameter of the outlet portion 25. However, for example, a plurality of annular protrusions are provided on the outer peripheral surface of the tubular member 101 at intervals. The external diameter of these annular protrusions may be larger than the internal diameter of the outlet portion 25.

The rod-shaped member 102 connected to the tubular member 101 has a length equal to or more than the length ranging from the opening of the inlet portion 24 of the treatment tool insertion channel 23 to the outlet portion 25 of the treatment tool insertion channel 23, and the tubular member 101 inserted into the treatment tool insertion channel 23 is capable of being pushed up to the outlet portion 25. The rod-shaped member 102 may have stiffness such that the tubular member 101 is capable of being pushed up to the outlet portion 25, and the material of the rod-shaped member 102 is not particularly limited.

Also, the rod-shaped member 102 is configured to be separable from the tubular member 101 fixed to the outlet portion 25 of the treatment tool insertion channel 23. In the example illustrated in FIG. 4, a constricted part 104 is formed at a distal end part of the rod-shaped member 102 connected to the tubular member 101. For example, as the constricted part 104 is threaded by rotating the rod-shaped member 102, the rod-shaped member 102 is separated from the tubular member 101. Although the tubular member 101 may be pushed into the outlet portion 25 by a rod-shaped member that is separate from the tubular member 101, the rod-shaped member 102 is configured integrally with the tubular member 101 so as to be separable from the tubular member 101. Accordingly, the handling of the endoscope aid 100 becomes easy.

The wire member 103 connected to the tubular member 101 has a length equal to or more than the length ranging from the tubular member 101 fixed to the outlet portion 25 of the treatment tool insertion channel 23 to the opening (inlet) of the inlet portion 24 of the treatment tool insertion channel 23 and is drawn out of the treatment tool insertion channel 23 through the opening of the inlet portion 24. As the wire member 103 is pulled out from the treatment tool insertion channel 23, the tubular member 101 is pulled by the wire member 103, and the tubular member 101 fixed to the outlet portion 25 is also pulled out from the treatment tool insertion channel 23. The wire member 103 may have a tensile strength such that the wire member 103 can withstand the frictional resistance in a case where the tubular member 101 is pulled out from the treatment tool insertion channel 23 and flexibility that does not hinder the bending of the bending part 15. The material of the wire member 103 is not particularly limited.

With reference to FIGS. 5 to 8, the outlet portion 25 of the treatment tool insertion channel 23 will be described.

As described above, the channel tube 43 constituting the treatment tool insertion channel 23 reaches the distal end part 14 of the insertion part 10 through the insides of the plurality of pieces 50 included in the bending part 15 and is joined to the distal end rigid part 40 of the distal end part 14, and the inner hole of the channel tube 43 communicates with the through-hole 42 of the distal end rigid part 40. Although the channel tube 43 is bent in accordance with the bending of the bending part 15, the outlet portion 25 of the treatment tool insertion channel 23 is a portion that is maintained in the shape of a straight pipe irrespective of the bending of the bending part 15.

Figure 5:
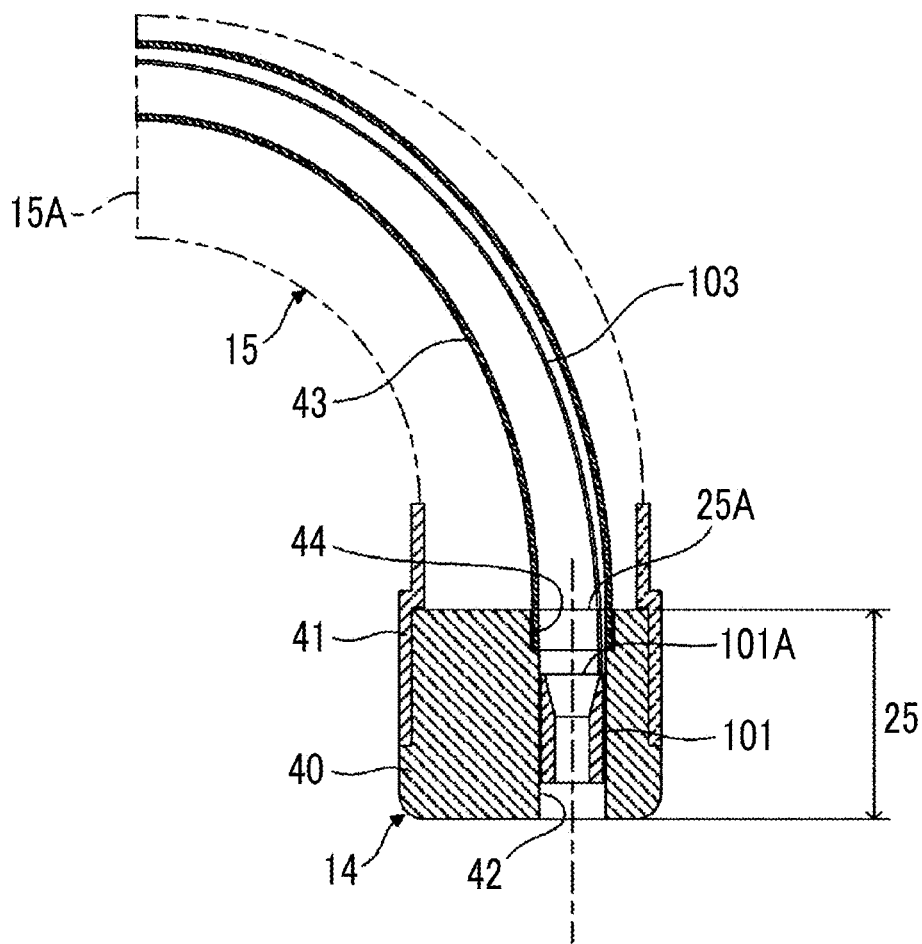
FIG. 5 is a cross-sectional view of an example of an outlet portion of a treatment tool insertion channel in a state where the endoscope aid of FIG. 4 is attached to the treatment tool insertion channel of the endoscope of FIG. 1.

In the example illustrated in FIG. 5, a fitting hole 44, which is coaxial with the through-hole 42 and has a larger diameter than the through-hole 42, is formed in a proximal end part of the distal end rigid part 40. A distal end of the channel tube 43 is internally fitted to the fitting hole 44 and is joined to the distal end rigid part 40 by bonding or the like. The through-hole 42 and the fitting hole 44 are maintained in the shape of a straight pipe irrespective of the bending of the bending part 15. In this case, the outlet portion 25 of the treatment tool insertion channel 23 is constituted of the through-hole 42 and the fitting hole 44.

Figure 6:
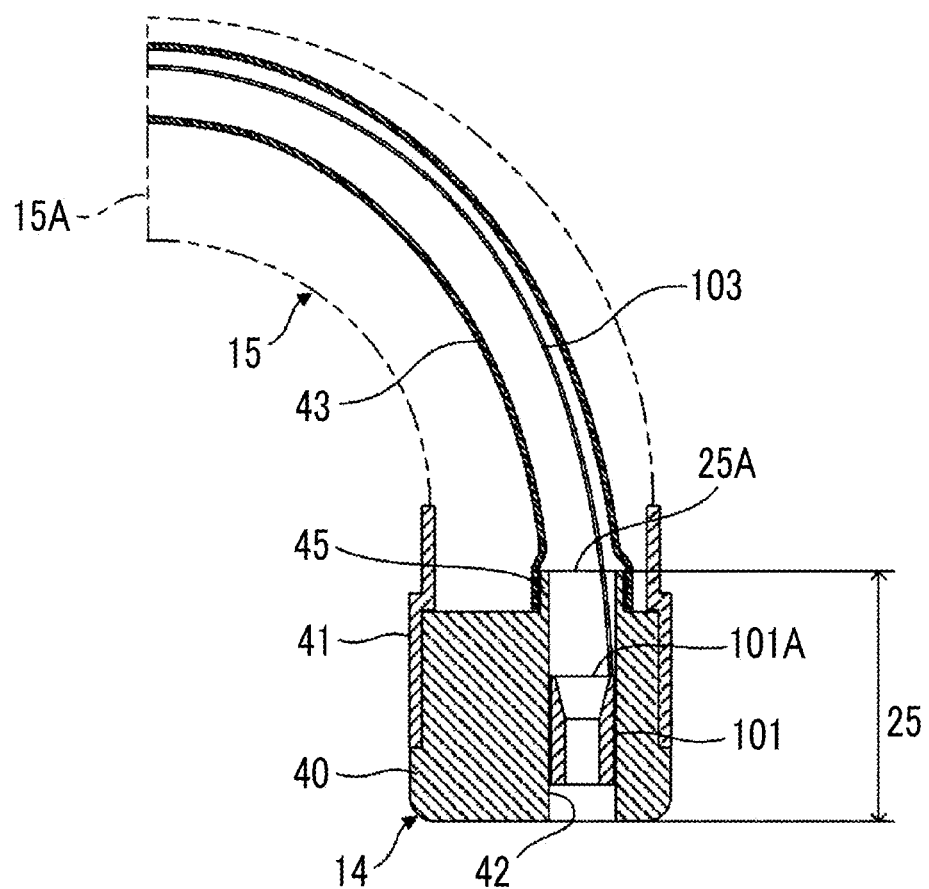
FIG. 6 is a cross-sectional view of another example of the outlet portion of the treatment tool insertion channel in the state where the endoscope aid of FIG. 4 is attached to the treatment tool insertion channel of the endoscope of FIG. 1.

In the example illustrated in FIG. 6, an annular protrusion 45, which is coaxial with the through-hole 42 and has the same internal diameter as the internal diameter of the through-hole 42, is formed in the proximal end part of the distal end rigid part 40 integrally with the distal end rigid part 40. The distal end of the channel tube 43 is externally fitted to the annular protrusion 45. The through-hole 42 and the annular protrusion 45 are maintained in the shape of a straight pipe irrespective of the bending of the bending part 15. In this case, the outlet portion 25 of the treatment tool insertion channel 23 is constituted of the through-hole 42 and the annular protrusion 45.

Figure 7:
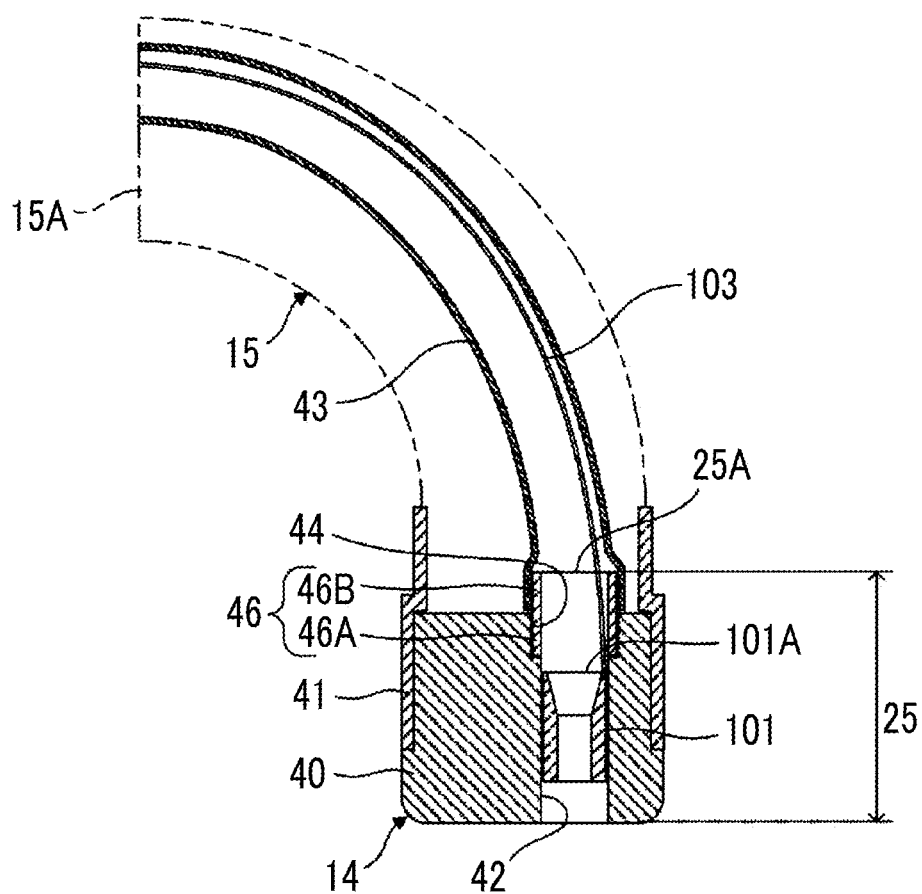
FIG. 7 is a cross-sectional view of still another example of the outlet portion of the treatment tool insertion channel in the state where the endoscope aid of FIG. 4 is attached to the treatment tool insertion channel of the endoscope of FIG. 1.

In the example illustrated in FIG. 7, a fitting hole 44, which is coaxial with the through-hole 42 and has a larger diameter than the through-hole 42, is formed in the proximal end part of the distal end rigid part 40, and a distal end part 46A of a hard connection pipe 46 that is a member separate from the distal end rigid part 40, is internally fitted the fitting hole 44. The distal end of the channel tube 43 is externally fitted to a proximal end part 46B of the connection pipe 46 protruding from the fitting hole 44. The through-hole 42, the fitting hole 44, and the connection pipe 46 are maintained in the shape of a straight pipe irrespective of the bending of the bending part 15. In this case, the outlet portion 25 of the treatment tool insertion channel 23 is constituted of the through-hole 42, the fitting hole 44, and the connection pipe 46.

Figure 8:
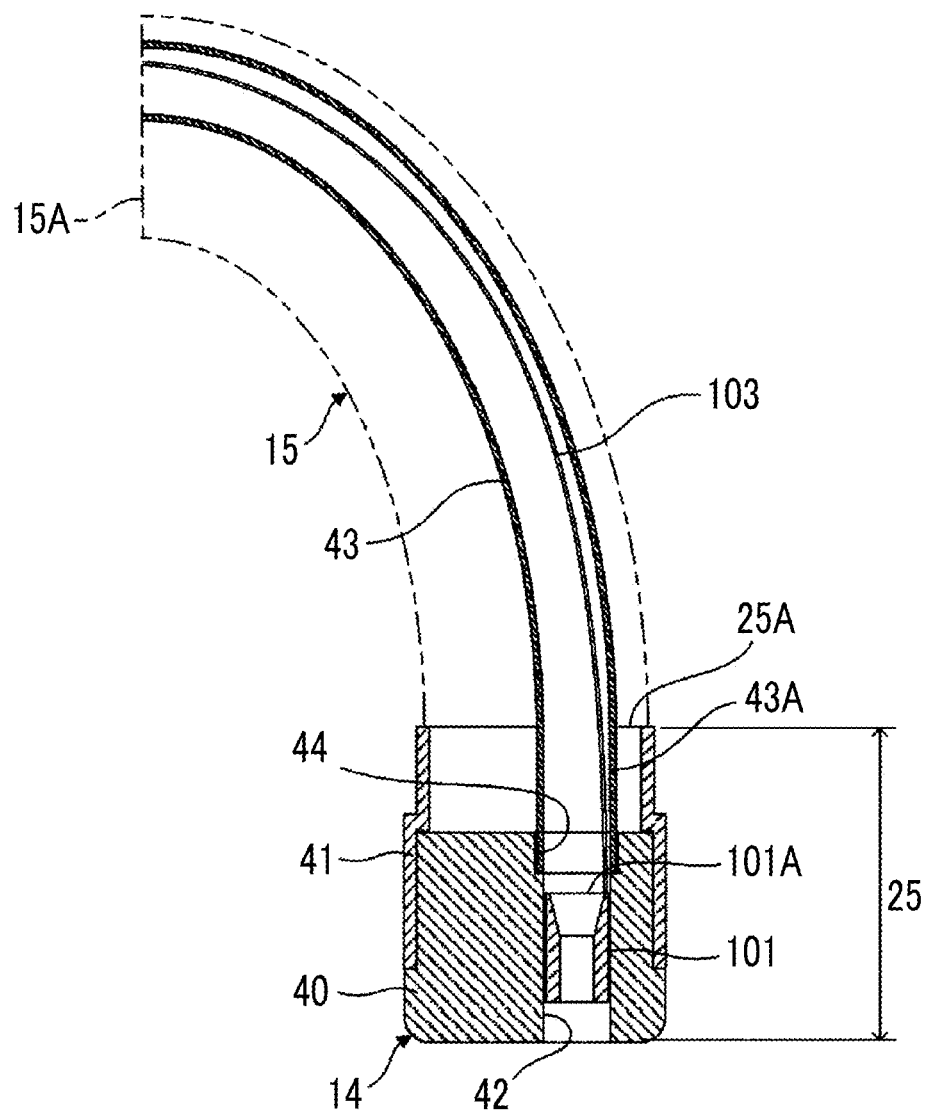
FIG. 8 is a cross-sectional view of a still further example of the outlet portion of the treatment tool insertion channel in the state where the endoscope aid of FIG. 4 is attached to the treatment tool insertion channel of the endoscope of FIG. 1.

In the example illustrated in FIG. 8, the maximum rotational movement angle of a set of two adjacent pieces 50 disposed nearest to the distal end part 14 side among the plurality of pieces 50 (refer to FIG. 3) included in the bending part 15 is extremely small, and a distal end part 43A of the channel tube 43 disposed inside the distal end sleeve 41 of the distal end part 14 is maintained in the shape of a straight pipe irrespective of the bending of the bending part 15. The outlet portion 25 of the treatment tool insertion channel 23 is constituted of the through-hole 42, the fitting hole 44, and the distal end part 43A of the channel tube 43.

In addition, whether or not the channel tube 43 is in the shape of straight pipe can be evaluated depending on the straightness of the channel tube 43 in the longitudinal axis, and in a case where the straightness of a portion to be evaluated in the longitudinal axis is 10% or less of the internal diameter of the channel tube 43, the portion to be evaluated is in the shape of a straight pipe. Additionally, in a case where two or more sets of two pieces 50 of which the maximum rotational movement angle is extremely small are continuously provided from the distal end part 14 side, there is a case where the outlet portion 25 reaches the insides of one or a plurality of pieces 50 disposed on the distal end part 14 side.

As illustrated in each of FIGS. 5 to 8, in a state where the tubular member 101 is fixed to the outlet portion 25 of the treatment tool insertion channel 23, a proximal end 101A of the tubular member 101 is located on a side opposite to the opening (outlet) side of the outlet portion 25 is disposed closer to the opening side of the outlet portion 25 than the proximal end 15A of the bending part 15. Accordingly, it is possible to suppress degradation of the bending performance of the bending part 15 due to the stiffness of the tubular member 101.

Preferably, the tubular member 101 has a length equal to or less than the length of the outlet portion 25 of the treatment tool insertion channel 23. In this case, the proximal end 101A of the tubular member 101 is disposed closer to the opening side of the outlet portion 25 than a proximal end 25A of the outlet portion 25 in a state where the tubular member 101 is fixed to the outlet portion 25. Accordingly, it is possible to further suppress the degradation of the bending performance of the bending part 15 due to the stiffness of the tubular member 101. In addition, a distal end of the tubular member 101 may reach, for example, the opening of the outlet portion 25 or may protrude from the opening of the outlet portion 25.

The above endoscope aid 100 is used in combination with a treatment tool with a smaller size than the internal diameter of the treatment tool insertion channel 23. The treatment tool is, for example, a puncturing needle, high-frequency scissors forceps, a high-frequency knife, bipolar hemostatic forceps, a clip, a collection net, or the like.

Figure 9:
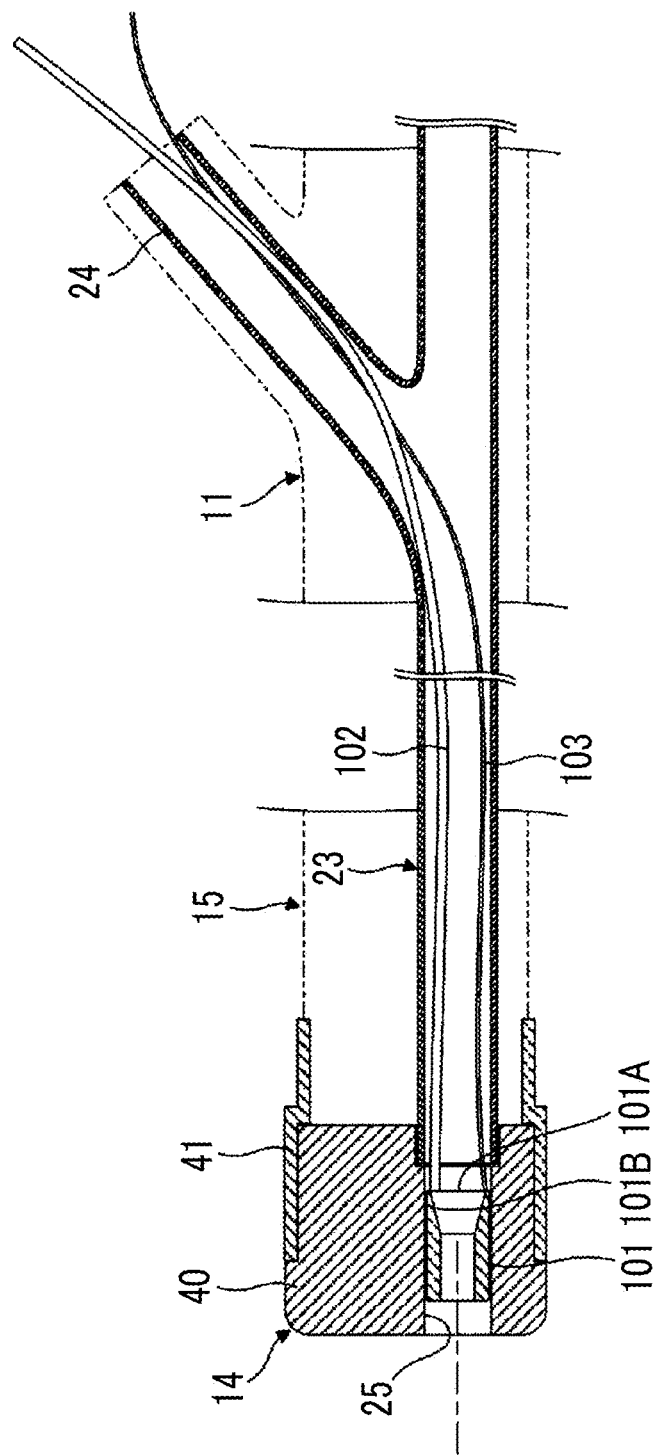
FIG. 9 is a schematic view illustrating a method of using the endoscope aid of FIG. 4.

First, as illustrated in FIG. 9, the tubular member 101 is inserted into the treatment tool insertion channel 23. In addition, the forceps valve 30 (refer to FIG. 2) mounted on the inlet portion 24 of the treatment tool insertion channel 23 is once detached from the inlet portion 24. The tubular member 101 is pushed into the outlet portion 25 of the treatment tool insertion channel 23 by the rod-shaped member 102 and fixed to the outlet portion 25. A central axis of an inner hole of the outlet portion 25, which is kept in the shape of a straight pipe regardless of the bending of the bending part 15 and a central axis of an inner hole of the tubular member 101 fixed to the outlet portion 25 are parallel to each other and coincide with each other in the present example.

Figure 10:
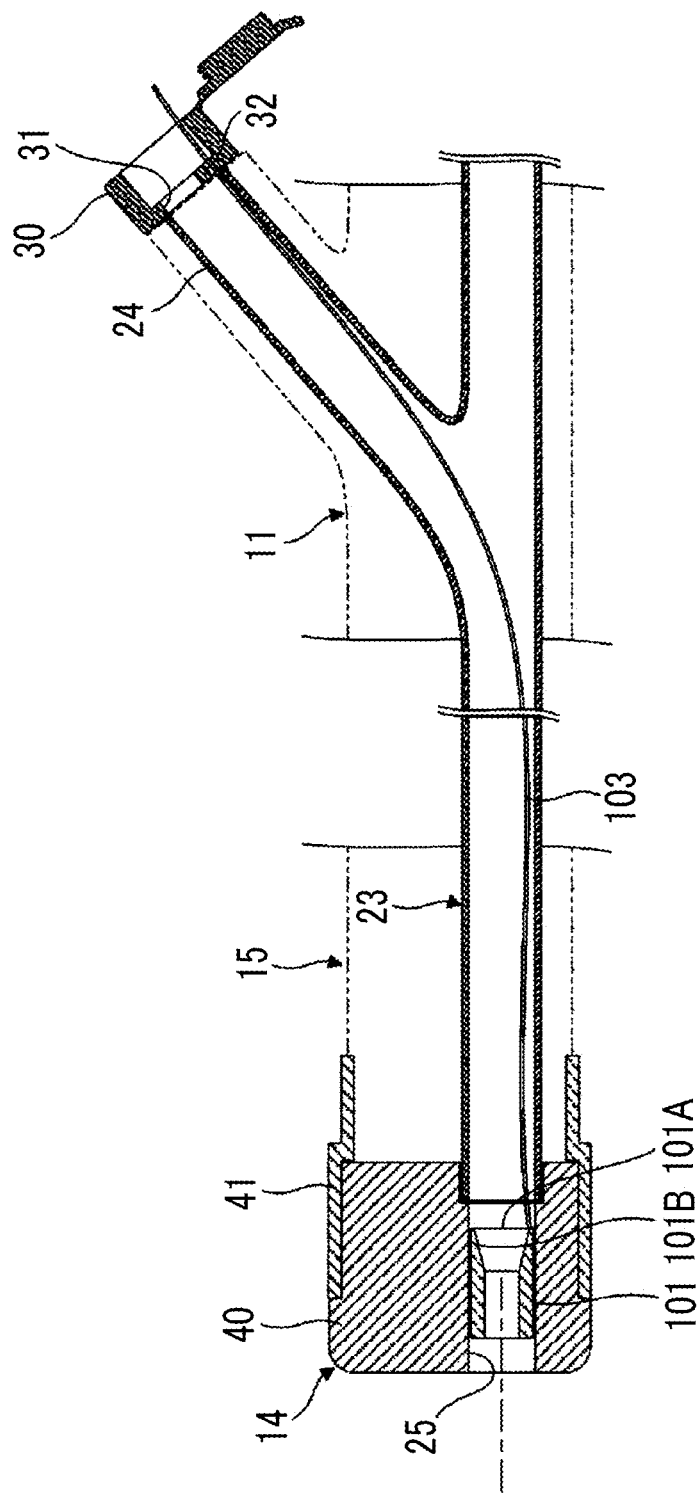
FIG. 10 is a schematic view illustrating the method of using the endoscope aid of FIG. 4.

Next, as illustrated in FIG. 10, after the tubular member 101 is fixed to the outlet portion 25, the rod-shaped member 102 is separated from the tubular member 101 and pulled out from the treatment tool insertion channel 23. The wire member 103 is left in the treatment tool insertion channel 23 and is drawn out of the treatment tool insertion channel 23 through the opening of the inlet portion 24 of the treatment tool insertion channel 23. The forceps valve 30 is mounted on the inlet portion 24 again in a state where the tubular member 101 and the wire member 103 have been installed. Preferably, the forceps valve 30 has a treatment tool insertion hole 31 and a wire insertion hole 32 formed separately from the treatment tool insertion hole 31, and the wire member 103 is drawn out of the treatment tool insertion channel 23 through the wire insertion hole 32. Accordingly, the treatment tool inserted through the treatment tool insertion hole 31 and the wire member 103 can be prevented from being entangled with each other.

Figure 11:
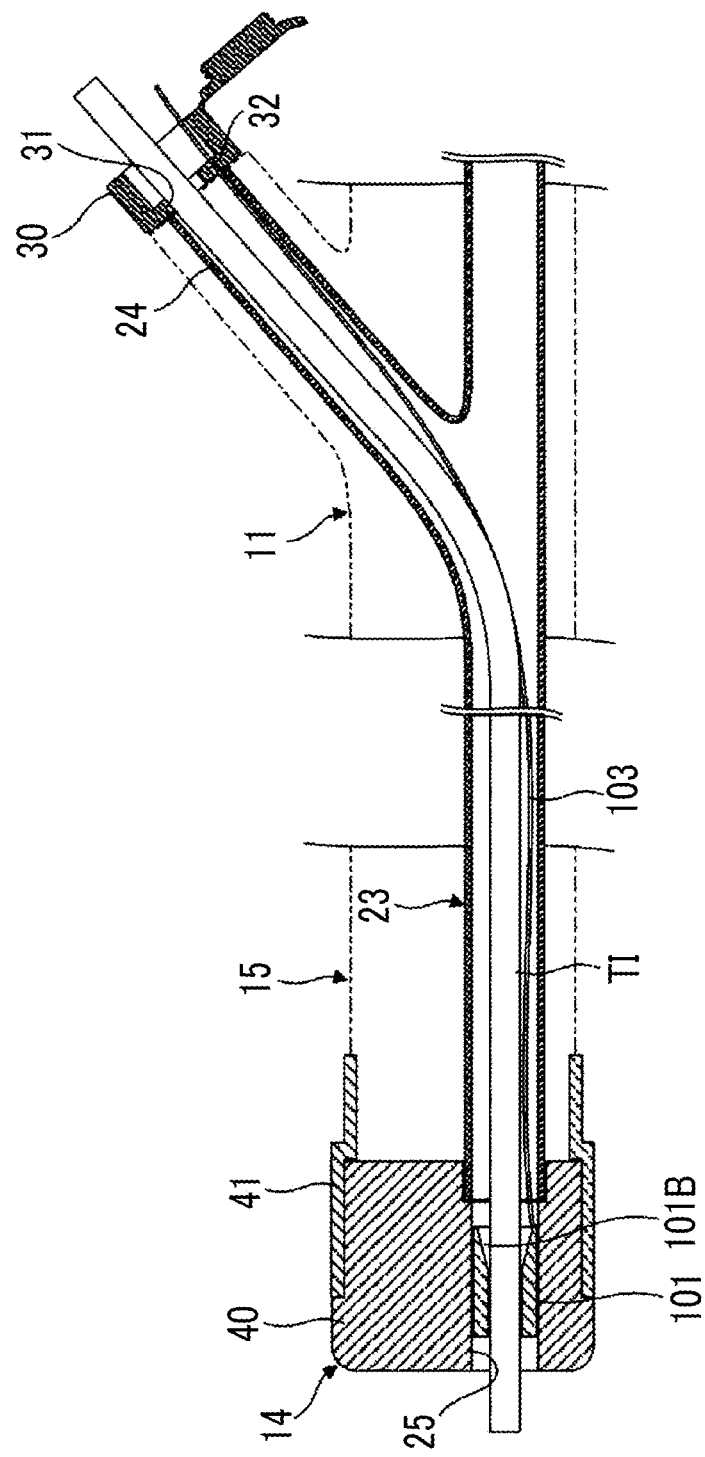
FIG. 11 is a schematic view illustrating the method of using the endoscope aid of FIG. 4.

Next, as illustrated in FIG. 11, a treatment tool TI is inserted into the treatment tool insertion channel 23. The treatment tool TI inserted into the treatment tool insertion channel 23 protrudes from the distal end part 14 of the insertion part 10 through the inner hole of the tubular member 101 fixed to the outlet portion 25 of the treatment tool insertion channel 23. Since the treatment tool TI protrudes onto the central axis of the inner hole of the tubular member 101 and the central axis of the inner hole of the tubular member 101 and the central axis of the inner hole of the outlet portion 25 are parallel to each other, the treatment tool TI protrudes along the central axis of the inner hole of the outlet portion 25. Accordingly, the disposition of the treatment tool TI is stable.

Preferably, an inner peripheral surface 101B of the tubular member 101 on the proximal end 101A side is formed in a tapered shape in which the diameter is gradually reduced toward the distal end side of the tubular member 101. Accordingly, the treatment tool TI can be smoothly inserted into the tubular member 101.

After the treatment using the treatment tool TI is completed, the treatment tool TI is pulled out from the treatment tool insertion channel 23, and then the wire member 103 is pulled out from the treatment tool insertion channel 23. By pulling out the wire member 103, the tubular member 101 is pulled by the wire member 103, and the tubular member 101 fixed to the outlet portion 25 of the treatment tool insertion channel 23 is also pulled out from the treatment tool insertion channel 23.

In this way, the tubular member 101 is attachably and detachably fitted and fixed to the inside of the outlet portion 25 of the treatment tool insertion channel 23 that is maintained in the shape of a straight pipe regardless of the bending of the bending part 15. Accordingly, the internal diameter of the treatment tool insertion channel 23 can be changed depending on situations, and the disposition of the treatment tool TI at the outlet portion 25 of the treatment tool insertion channel 23 can be stabilized. Also, in a case where the tubular member 101 is fixed to the outlet portion 25, the proximal end 101A of the tubular member 101 is disposed closer to the opening side of the outlet portion 25 of the treatment tool insertion channel 23 than the proximal end 15A of the bending part 15. Accordingly, it is possible to suppress the degradation of the bending performance of the bending part 15 due to the stiffness of the tubular member 101.

Figure 12:
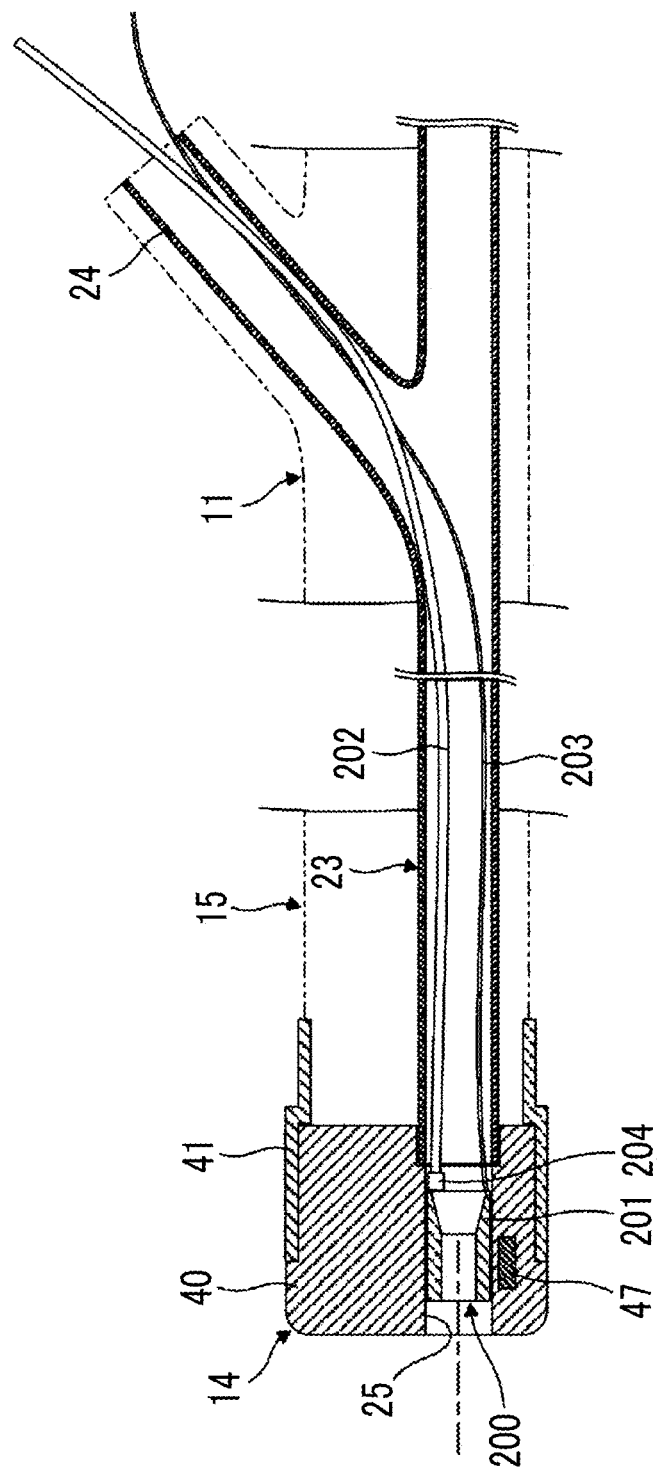
FIG. 12 is a cross-sectional view illustrating another example of the endoscope aid for explaining the embodiment of the present invention and an example of an outlet portion of the treatment tool insertion channel illustrating a state in which the endoscope aid is attached to the treatment tool insertion channel of the endoscope of FIG. 1.

FIG. 12 illustrates another example of the endoscope aid for explaining the embodiment of the present invention.

An endoscope aid 200 illustrated in FIG. 12 includes a tubular member 201 having a circular cross-sectional shape, a rod-shaped member 202 connected to a proximal end part of the tubular member 201, and a wire member 203 connected to the proximal end part of the tubular member 201.

The tubular member 201 is a magnetic body containing a magnetic material such as iron or cobalt or a powder of the magnetic material. The magnetic body containing the powder of the magnetic material may be one obtained by baking the powder of the magnetic material or one obtained by the powder of the magnetic material being bonded together with a resin binder. The tubular member 201 is s fixed to the outlet portion 25 in a state where the tubular member 201 is inserted into the treatment tool insertion channel 23 through the opening of the inlet portion 24 of the treatment tool insertion channel 23 and is fitted inside the outlet portion 25 of the treatment tool insertion channel 23. A magnet 47 is provided on a distal end rigid part 40 of the distal end part 14 of the insertion part 10, and the tubular member 201, which is a magnetic body, is fixed to the outlet portion 25 by being attracted by the magnet 47. In addition, at least a portion of the tubular member 201 may be a magnetic body.

The rod-shaped member 202 connected to the proximal end part of the tubular member 201 is configured to be capable of pushing the tubular member 201 inserted into the treatment tool insertion channel 23 up to the outlet portion 25 and separable from the tubular member 201 fixed to the outlet portion 25. In the example illustrated in FIG. 12, a magnet 204 is provided at a distal end part of the rod-shaped member 202, and a magnetic force (attractive force) generated between the magnet 204 and the tubular member 201 is smaller than a magnetic force (attractive force) generated between the magnet 47, which fixes the tubular member 201 to the outlet portion 25, and the tubular member 201. The rod-shaped member 202 is separated from the tubular member 201 by pulling the rod-shaped member 202 in a state where the tubular member 201 is fixed to the outlet portion 25.

The wire member 203 connected to the tubular member 201 is drawn out to the outside of the treatment tool insertion channel 23 through the opening of the inlet portion 24 of the treatment tool insertion channel 23 from the tubular member 201 fixed to the outlet portion 25 of the treatment tool insertion channel 23. By pulling out the wire member 203 from the treatment tool insertion channel 23, the tubular member 201 fixed to the outlet portion 25 is also pulled out from the treatment tool insertion channel 23.

In this way, in a case where the tubular member 201 is fixed to the outlet portion 25 of the treatment tool insertion channel 23 by the magnetic force, the external diameter of the tubular member 201 can be set to be smaller than the internal diameter of the outlet portion 25, and the tubular member 201 can be fitted inside the outlet portion 25 in a so-called clearance fit state. Accordingly, the frictional resistance in a case where the tubular member 201 is pushed into the treatment tool insertion channel 23 and is pulled from the treatment tool insertion channel 23, can be reduced, and handling of the endoscope aid 200 can be made easier.

As described above, an endoscope aid disclosed in the present specification is an endoscope aid to be attachably and detachably attached to a treatment tool insertion channel of an endoscope. The endoscope aid comprises a tubular member capable of being fixed to an outlet portion of the treatment tool insertion channel in a state where the tubular member is fitted inside the outlet portion of the treatment tool insertion channel that is kept in the shape of a straight pipe regardless of bending of a bending part of the endoscope. When the tubular member is fixed to the outlet portion of the treatment tool insertion channel, a proximal end of the tubular member located on a side opposite to an outlet side of the treatment tool insertion channel is disposed closer to the outlet side of the treatment tool insertion channel than a proximal end of the bending part of the endoscope.

Additionally, in the endoscope aid disclosed in the present specification, the tubular member has a length less than a length of the outlet portion of the treatment tool insertion channel.

Additionally, in the endoscope aid disclosed in the present specification, an inner peripheral surface of the tubular member on the proximal end side is formed in a tapered shape in which a diameter is gradually reduced toward a distal end side.

Additionally, the endoscope aid disclosed in the present specification further comprises a wire member connected to the tubular member. The wire member has a length equal to or more than a length ranging from the tubular member fixed to the outlet portion of the treatment tool insertion channel to an inlet of the treatment tool insertion channel.

Additionally, the endoscope aid disclosed in the present specification further comprises a rod-shaped member connected to the tubular member. The rod-shaped member is capable of being pushed to the outlet portion of the treatment tool insertion channel through an inlet of the treatment tool insertion channel and is separable from the tubular member fixed to the outlet portion.

Additionally, in the endoscope aid disclosed in the present specification, the tubular member is an elastic body, and an external diameter of at least a portion of the tubular member in an axial direction is larger than an internal diameter of the outlet portion of the treatment tool insertion channel.

Additionally, in the endoscope aid disclosed in the present specification, at least a portion of the tubular member is a magnetic body and is fixed to the outlet portion of the treatment tool insertion channel by a magnetic force.

Additionally, an endoscope disclosed in the present specification comprises a treatment tool insertion channel to which the endoscope aid is attachable.

EXPLANATION OF REFERENCES

1: endoscope system
2: endoscope
3: light source device
4: processor unit
5: suction pump
6: monitor
10: insertion part
11: operating part
12: universal cord
13: connector
14: distal end part of insertion part
15: bending part of endoscope
15A: proximal end of bending part
16: flexible part
17: imaging unit
18A, 18C: operation button
18B: operating knob
20: light guide
21: electrical cable
22, 22A, 22B: operating wire
23: treatment tool insertion channel
24: inlet portion
25: outlet portion
25A: proximal end of outlet portion
26: suction tube
27: valve
28: mouthpiece
29: connection tube
30: forceps valve
31: treatment tool insertion hole
32: wire insertion hole
40: distal end rigid part
41: distal end sleeve
42: through-hole
43: channel tube
43A: distal end part of channel tube
44: fitting hole
45: annular protrusion
46: connection pipe
46A: distal end part of connection pipe
46B: proximal end part of connection pipe
47: magnet
50: piece
51: shaft member
100, 200: endoscope aid
101, 201: tubular member
101A: proximal end of tubular member
101B: inner peripheral surface on proximal end side of tubular member
102, 202: rod-shaped member
103, 203: wire member
104: constricted part
204: magnet
Gx, Gy: spacing
TI: treatment tool
X, Y: rotational movement axis

What is claimed is:

1. An endoscope aid to be attachably and detachably attached to a treatment tool insertion channel of an endoscope, the endoscope aid comprising:
    a tubular member capable of being fixed to an outlet portion of the treatment tool insertion channel in a state where the tubular member is fitted inside the outlet portion of the treatment tool insertion channel that is kept in the shape of a straight pipe regardless of bending of a bending part of the endoscope,
    wherein when the tubular member is fixed to the outlet portion of the treatment tool insertion channel, a proximal end of the tubular member located on a side opposite to an outlet side of the treatment tool insertion channel is disposed closer to the outlet side of the treatment tool insertion channel than a proximal end of the bending part of the endoscope,
    wherein an inner peripheral surface of the tubular member on the proximal end side is formed in a tapered shape in which a diameter is gradually reduced toward a distal end side,
    wherein the outlet portion comprises a through-hole, and an entire diameter of the through-hole in an axial direction is constant,
    wherein a distal end of a channel tube of the treatment tool insertion channel is fitted to the outlet portion, and the channel tube has an external diameter less than that of the outlet portion,
    wherein when the entire tubular member is fitted inside the through-hole, a proximal end of the outlet portion is disposed between the proximal end of the bending part and the proximal end of the tubular member, and the distal end of the channel tube is disposed between the proximal end of the outlet portion and the proximal end of the tubular member,
    wherein the tubular member is spaced apart from the channel tube by a gap therebetween.

2. The endoscope aid according to claim 1, wherein the tubular member has a length less than a length of the outlet portion of the treatment tool insertion channel.

3. The endoscope aid according to claim 2, further comprising:
   a wire member connected to the tubular member,
   wherein the wire member has a length equal to or more than a length ranging from the tubular member fixed to the outlet portion of the treatment tool insertion channel to an inlet of the treatment tool insertion channel.

4. The endoscope aid according to claim 3, further comprising:
   a rod-shaped member connected to the tubular member,
   wherein the rod-shaped member is capable of being pushed to the outlet portion of the treatment tool insertion channel through the inlet of the treatment tool insertion channel and is separable from the tubular member fixed to the outlet portion.

5. The endoscope aid according to claim 4,
   wherein the tubular member is an elastic body, and
   an external diameter of at least a portion of the tubular member in an axial direction is larger than an internal diameter of the outlet portion of the treatment tool insertion channel.

6. The endoscope aid according to claim 3,
   wherein the tubular member is an elastic body, and
   an external diameter of at least a portion of the tubular member in an axial direction is larger than an internal diameter of the outlet portion of the treatment tool insertion channel.

7. The endoscope aid according to claim 2, further comprising:
   a rod-shaped member connected to the tubular member,
   wherein the rod-shaped member is capable of being pushed to the outlet portion of the treatment tool insertion channel through an inlet of the treatment tool insertion channel and is separable from the tubular member fixed to the outlet portion.

8. The endoscope aid according to claim 7,
   wherein the tubular member is an elastic body, and
   an external diameter of at least a portion of the tubular member in an axial direction is larger than an internal diameter of the outlet portion of the treatment tool insertion channel.

9. The endoscope aid according to claim 2,
   wherein the tubular member is an elastic body, and
   an external diameter of at least a portion of the tubular member in an axial direction is larger than an internal diameter of the outlet portion of the treatment tool insertion channel.

10. The endoscope aid according to claim 2,
    wherein at least a portion of the tubular member is a magnetic body and is fixed to the outlet portion of the treatment tool insertion channel by a magnetic force.

11. The endoscope aid according to claim 1, further comprising:
    a wire member connected to the tubular member,
    wherein the wire member has a length equal to or more than a length ranging from the tubular member fixed to the outlet portion of the treatment tool insertion channel to an inlet of the treatment tool insertion channel.

12. The endoscope aid according to claim 11, further comprising:
    a rod-shaped member connected to the tubular member,
    wherein the rod-shaped member is capable of being pushed to the outlet portion of the treatment tool insertion channel through the inlet of the treatment tool insertion channel and is separable from the tubular member fixed to the outlet portion.

13. The endoscope aid according to claim 12,
    wherein the tubular member is an elastic body, and
    an external diameter of at least a portion of the tubular member in an axial direction is larger than an internal diameter of the outlet portion of the treatment tool insertion channel.

14. The endoscope aid according to claim 11,
    wherein the tubular member is an elastic body, and
    an external diameter of at least a portion of the tubular member in an axial direction is larger than an internal diameter of the outlet portion of the treatment tool insertion channel.

15. The endoscope aid according to claim 11,
    wherein at least a portion of the tubular member is a magnetic body and is fixed to the outlet portion of the treatment tool insertion channel by a magnetic force.

16. The endoscope aid according to claim 1, further comprising:
    a rod-shaped member connected to the tubular member,
    wherein the rod-shaped member is capable of being pushed to the outlet portion of the treatment tool insertion channel through an inlet of the treatment tool insertion channel and is separable from the tubular member fixed to the outlet portion.

17. The endoscope aid according to claim 16,
    wherein the tubular member is an elastic body, and
    an external diameter of at least a portion of the tubular member in an axial direction is larger than an internal diameter of the outlet portion of the treatment tool insertion channel.

18. The endoscope aid according to claim 1,
    wherein the tubular member is an elastic body, and
    an external diameter of at least a portion of the tubular member in an axial direction is larger than an internal diameter of the outlet portion of the treatment tool insertion channel.

19. The endoscope aid according to claim 1,
    wherein at least a portion of the tubular member is a magnetic body and is fixed to the outlet portion of the treatment tool insertion channel by a magnetic force.

20. An endoscope comprising:
    a treatment tool insertion channel to which the endoscope aid according to claim 1 is attachable.

* * * * *